United States Patent [19]
Igaue et al.

[11] Patent Number: 5,820,617
[45] Date of Patent: Oct. 13, 1998

[54] DISPOSABLE DIAPER

[75] Inventors: Takamitsu Igaue; Toru Sasaki, both of Ehime-ken, Japan

[73] Assignee: Uni-Charm Corporation, Ehime-ken, Japan

[21] Appl. No.: 783,140

[22] Filed: Jan. 14, 1997

[30] Foreign Application Priority Data

Jan. 26, 1996 [JP] Japan .................................. 8-012053

[51] Int. Cl.⁶ .................................................. A61F 13/15
[52] U.S. Cl. ........................................ 604/385.1; 604/389
[58] Field of Search .................................. 604/358, 383, 604/367, 385.1, 385.2, 389

[56] References Cited

U.S. PATENT DOCUMENTS

| | | | |
|---|---|---|---|
| 3,867,940 | 2/1975 | Mesek et al. ........................... | 604/390 |
| 4,352,355 | 10/1982 | Mesek et al. ........................... | 604/385.2 |
| 4,916,005 | 4/1990 | Lippert et al. ........................... | 604/383 |
| 5,569,234 | 10/1996 | Buell et al. ............................... | 604/358 |
| 5,571,096 | 11/1996 | Dobrin et al. ........................... | 604/383 |

FOREIGN PATENT DOCUMENTS

| | | |
|---|---|---|
| 3-86159 | 4/1991 | Japan . |
| 2 180 456 | 9/1985 | United Kingdom . |
| 2 286 558 | 2/1994 | United Kingdom . |

*Primary Examiner*—Robert A. Clarke
*Attorney, Agent, or Firm*—Lowe Hauptman Gopstein Gilman & Berner

[57] ABSTRACT

A backsheet of a disposable diaper comprises a plastic film covering an entire outer side of the diaper and a pair of nonwoven fabrics laminated to an outer surface of the plastic film over front and rear waist region but longitudinally spaced apart from each other over a crotch region.

6 Claims, 1 Drawing Sheet

DISPOSABLE DIAPER

BACKGROUND OF THE INVENTION

The present invention relates generally to a disposable diaper for absorption and containment of urine and other body exudates.

It is well known to use a liquid-impermeable plastic film such as polyethylene film as a liquid-impermeable backsheet of a disposable diaper. It is also known from, for example, Japanese Laid-Open Patent Application No. Hei3-86159 to use a composite sheet composed of a plastic film and a nonwoven fabric laminated to an outer surface of the plastic film as the backsheet.

A diaper of using a plastic film as the backsheet is generally disliked by users thereof due to uncomfortable touch peculiar to the plastic film. Use of a composite sheet composed of such a film and a nonwoven fabric covering an outer surface of the film as disclosed in the aboveidentified application certainly eliminates the problem peculiar to a plastic film by providing an outer surface of the diaper with a cloth-like touch. However, the backsheet made of such a composite sheet necessarily has a rigidity higher than that of a backsheet made of a plastic film alone and pitches of gathers formed around a waist opening as well as leg openings, respectively, as elastic members provided around those openings contract, become correspondingly rough. When gathers formed around the leg openings are of a rough pitch, in other words, when gathers of a sufficiently fine pitch can not be obtained around the leg openings, a fitness of the diaper around the legs of a wearer will be deteriorated and, resulting in an undesirable leakage of body exudates around the leg openings.

SUMMARY OF THE INVENTION

In view of the problems as described above, it is a principal object of the invention to provide a disposable diaper arranged so that a soft touch feeling can be provided around a waist of a wearer and a fitness of the diaper around the legs of a wearer may be improved.

The object set forth above is achieved, according to the invention, by a disposable diaper having front and rear waist regions and a crotch region therebetween, the diaper comprising a liquid-permeable topsheet, a liquid-impermeable backsheet and a liquid-absorbent core disposed therebetween, and the crotch region being provided along transversely opposite side portions thereof with elastically stretchable members adopted to surround each leg of a wearer, wherein the backsheet comprises a liquid-impermeable plastic film and a pair of nonwoven fabrics comprising thermoplastic synthetic fibers integrally laminated to an outer surface of the plastic film over the front and rear waist regions respectively, but spaced apart from each other over the crotch region.

With the diaper of the invention, the outermost surfaces of the front and rear regions can offer agreeable cloth-like touch, on one hand, and the crotch region can form fine gathers and thereby ensure a fitness around the wearer's legs, on the other hand.

DESCRIPTION OF PREFERRED EMBODIMENT

Figure 1:
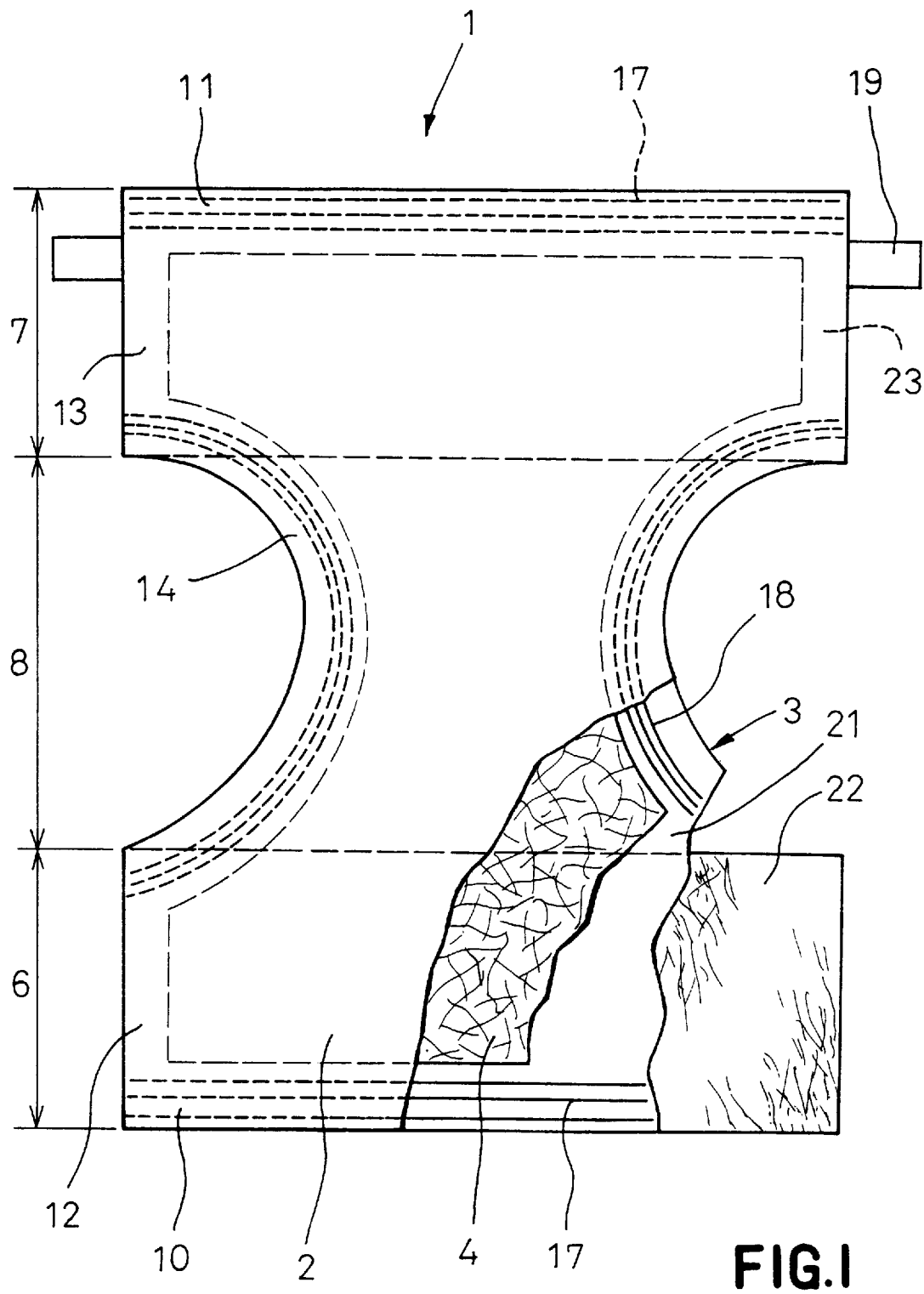
FIG. 1 is a plan view showing a disposable diaper of the invention as partially broken away.

A diaper 1 shown by FIG. 1 in a plan view as partially broken away comprises a liquid-permeable topsheet 2 intended to be contacted with the skin of a wearer, a liquid-impermeable backsheet 3 intended to be non-contacted with the skin and a liquid-absorbent core 4 disposed therebetween. The diaper 1 has a front waist region 6, a rear waist region 7 and a crotch region 8 extending therebetween. The topsheet 2 and the backsheet 3 are bonded together along portions thereof extending outward beyond a peripheral edge of the core 4 to define longitudinal end portions 10, 11 of the front and rear waist regions 6, 7, transversely opposite side edge portions 12 and 13 of the front and rear waist regions 6, 7, and transversely opposite side edge portions 14 of the crotch region 8, respectively. Both side edge portions 14 of the crotch region 8 are curved inwardly of the diaper 1 so as to fit around the legs of a wearer. The longitudinal end portions 10, 11 of the front and rear waist regions 6, 7 and the side edge portions 14 of the crotch region 8 are provided with elastic members 17 for the waist opening and elastic members 18 for the leg openings, respectively. These elastic members 17, 18 are disposed between the topsheet 2 and backsheet 3 and secured to any one of these sheets 2, 3 in elastically stretched conditions of them. A pair of tape fasteners 19 adapted to be detachably fastened to the side edge portions 12 of the front waist region 6 laterally extend from the side edge portions 13 of the rear waist region 7, respectively.

The topsheet 2 may be of a liquid-permeable nonwoven fabric of thermoplastic fibers or a liquid-permeable perforated plastic film.

The backsheet 3 comprises a liquid-impermeable or air-permeable but liquid-impermeable plastic film 21 covering the entire outer side of the diaper 1, a nonwoven fabric 22 of thermoplastic fibers substantially identical to the front waist region 6 in a shape as well as in a size thereof and integrally laminated to the plastic film 21 over the front waist region 6 and a nonwoven fabric 23 of thermoplastic fibers substantially identical to the rear waist region 7 in a shape as well as in a size thereof and integrally laminated to the plastic film 21 over the rear waist region 7. The nonwoven fabrics 22, 23 are of well-known ones in the art, but preferably melt-blown or spun laced ones in which a chemical bonding material is not used.

Of the backsheet 3 for the diaper 1, the front and rear waist regions 6, 7 adopted to be frequently contacted by hands of a wearer and his or her mother have the outermost surface provided with the nonwoven fabrics 22, 23 which offer soft and agreeable cloth-like touch. The crotch region 8 rarely contacted by the wearer and mother is constituted of the plastic film 21 alone and the absence of the nonwoven fabrics 22, 23 correspondingly reduces rigidity of the backsheet 3 in the crotch region 8 in comparison with the backsheet in the front and rear waist regions 6, 7. Consequently, relatively fine gathers can be formed along the transversely opposite side edge portions 14 of the crotch region 8 as the elastic members 18 contract, and such fine gathers ensure a fitness of the diaper 1 around the wearer's legs. With the diaper 1 being in its developed state, the nonwoven fabrics 22, 23 are longitudinally spaced apart from each other preferably by a range of 100–500 mm which may be appropriately increased in the case of an adult diaper. Laminating of the nonwoven fabrics 22, 23 to the plastic film 21 may be achieved by an adhesive such as a hot melt type adhesive or heat-sealing just as for bonding or jointing of other components of the diaper 1.

Although not shown, the nonwoven fabrics 22, 23 may be different from each other in their shapes as well as their sizes.

What is claimed is:

1. A disposable diaper having a front waist region, a rear waist region and a crotch region therebetween, said diaper comprising:

a liquid-permeable topsheet;

a liquid-impermeable backsheet;

a liquid-absorbent core disposed between said topsheet and said backsheet;

said backsheet comprising a liquid-impermeable plastic film and a pair of nonwoven fabrics integrally laminated to an outer surface of the plastic film over said front and rear waist regions, respectively, with said nonwoven fabrics being spaced apart from each other longitudinally of said diaper and occupying at least a longitudinally extending major area of a central portion of said front and rear waist regions;

transversely opposite side edge portions of said crotch region being curved inwardly of said diaper between said pair of nonwoven fabrics; and elastically stretchable members being provided along said transversely opposite side edge portions of said crotch region of a wearer and adapted to surround each leg of the wearer.

2. The disposable diaper according to claim 1, wherein said nonwoven fabrics are made of melt-blown or spun laced fabrics.

3. The disposable diaper according to claim 1, wherein said plastic film is air-permeable but liquid-impermeable.

4. The disposable diaper of claim 1, wherein each of said nonwoven fabrics occupies substantially the entire area of said front and rear waist regions, respectively.

5. A disposable diaper having a front waist region, a rear waist region and a crotch region therebetween, said diaper comprising:

a liquid-permeable topsheet;

a backsheet including a liquid-impermeable plastic film and a pair of nonwoven fabrics integrally laminated to an outer surface of the plastic film over said front and rear waist regions with said nonwoven fabrics being spaced apart from each other longitudinally of said diaper and occupying at least a longitudinally extending major area of a central portion of said front and rear waist regions;

a liquid-absorbent core disposed between said topsheet and said backsheet; and elastically stretchable members provided along said transversely opposite side edge portions of said crotch region.

6. The disposable diaper of claim 5, wherein each of said nonwoven fabrics occupies substantially the entire area of said front and rear waist regions, respectively.

* * * * *